United States Patent [19]

Deushi et al.

[11] 4,312,858
[45] Jan. 26, 1982

[54] ANTIBIOTIC KA-7038 AND COMPOSITIONS CONTAINING SAME

[75] Inventors: Takeo Deushi; Akio Iwasaki; Kazuhiro Kamiya; Toshimi Mizoguchi; Masahito Nakayama, all of Higashimurayama; Hisakatsu Itoh, Kawagoe; Toshihito Mori, Higashimurayama, all of Japan

[73] Assignee: Kowa Company, Ltd., Nagoya, Japan

[21] Appl. No.: 56,313

[22] Filed: Jul. 10, 1979

[30] Foreign Application Priority Data

Jul. 13, 1978 [JP] Japan .................................. 53-84537
Jun. 6, 1979 [JP] Japan .................................. 54-69877

[51] Int. Cl.$^3$ ........................ A61K 31/71; C07H 15/22
[52] U.S. Cl. .................................... 424/181; 424/180; 536/17 R
[58] Field of Search ........................... 536/17 R, 17 B; 424/180, 181

[56] References Cited

U.S. PATENT DOCUMENTS

| | | | |
|---|---|---|---|
| 3,931,400 | 1/1976 | Nara et al. | 424/118 |
| 3,976,768 | 8/1976 | Nara et al. | 424/118 |
| 4,145,253 | 3/1979 | Iida et al. | 260/345.9 R |
| 4,169,198 | 9/1979 | Martin et al. | 536/17 R |
| 4,176,178 | 11/1979 | Martin et al. | 536/17 R |
| 4,209,612 | 6/1980 | Takahashi et al. | 536/17 B |

FOREIGN PATENT DOCUMENTS

| | | | |
|---|---|---|---|
| 50-145588 | 11/1975 | Japan | 536/17 R |
| 52-83513 | 7/1977 | Japan | 536/17 R |

OTHER PUBLICATIONS

Egan, et al. "The Jour. of Antibiotics", vol. XXX, No. 7, pp. 552–563, Jul. 1977.

Primary Examiner—Johnnie R. Brown
Attorney, Agent, or Firm—Wenderoth, Lind & Ponack

[57] ABSTRACT

An antibiotic substance KA-7038 selected from the group consisting of the compounds having formulae I to VII described in claim 1, mixtures thereof and acid addition salts thereof; an antibiotic composition composed of (i) antibiotically effective amount of aforesaid antibiotic substance KA-7038, and (ii) a pharmaceutically acceptable diluent or carrier. The antibiotic substance KA-7038 can be produced by cultivating an antibiotic substance KA-7038-producing strain belonging to genus Streptomyces, for example Streptomyces sp. KC-7038, and isolating the antibiotic substance KA-7038 from the culture broth.

5 Claims, 7 Drawing Figures

ANTIBIOTIC KA-7038 AND COMPOSITIONS CONTAINING SAME

This invention relates to novel antibiotics, a process for preparation thereof, and a biologically pure culture for use in the process.

The present inventors have succeeded in isolating an antibiotic-producing strain belonging to the genus Streptomyces from the soil at Sannan-cho, Hikami-gun, Hyogo Prefecture, Japan. From its morphological, cultural and physiological characteristics described hereinbelow, the strain was assumed to be a novel species belonging to the genus Streptomyces, and termed Streptomyces sp. KC-7038. This strain KC-7038 was deposited as FERM-P No. 4388 in Fermentation Research Institute, Agency of Industrial Science & Technology, Japan; as ATCC number 31530 in American Type Culture Collection.

It has been ascertained that the antibiotics produced by the strain KC-7038 are substances not described in the literature and having an antibacterial action against Gram-positive bacteria and Gram-negative bacteria. This substance was termed "substance KA-7038".

Further investigations have led to the discovery that the substance KA-7038 can be further separated into seven antibiotics, KA-7038I, KA-7038II, KA-7038III, KA-7038IV, KA-7038V, KA-7038VI and KA-7038VII, and they can be readily converted to acid addition salts thereof by treatment with acids.

It is an object of this invention therefore to provide a novel antibiotic substance KA-7038 and its acid addition salts.

Another object of this invention is to provide a process for preparing the substance KA-7038.

Still another object of this invention is to provide an antibiotic composition containing the substance KA-7038 as an active ingredient.

A further object of the invention is to provide a biologically pure culture useful for providing the substance KA-7038.

The above and other objects of this invention along with its advantages will become more apparent from the following description.

The antibiotic substance KA-7038 of this invention can be expressed by the following structural formulas I to VII.

Substance KA-7038I formula I

Figure 1:
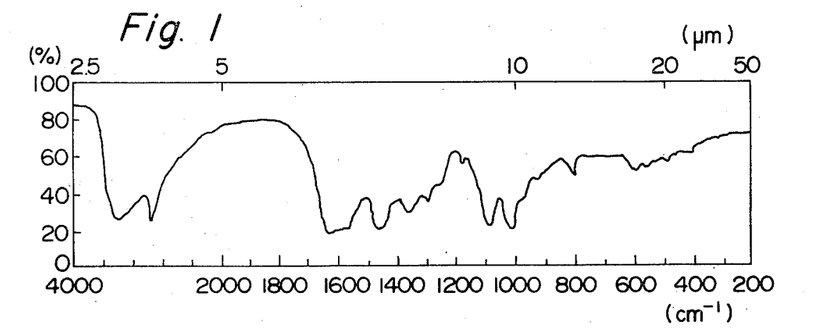

The chemical and physical properties of the substance KA-7038I are described below.
Molecular formula: $C_{17}H_{35}O_5N_5$
Specific rotation: $[\alpha]_D^{25} +120.5°$ (c 1, $H_2O$).
Melting point: 83°–90° C.
IR spectrum: FIG. 1.

Substance KA-7038II formula II

Figure 2:
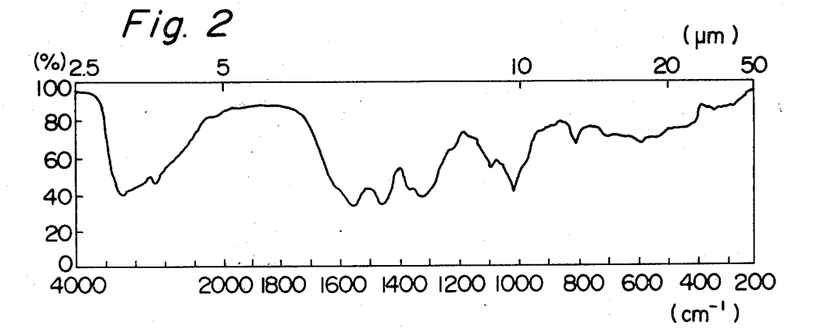

The chemical and physical properties of the substance KA-7038II are described below.
Molecular formula: $C_{13}H_{28}O_4N_4$
Specific rotation: $[\alpha]_D^{25} +61°$ (c 1, $H_2O$)
Melting point: 85°–102° C.
IR spectrum: FIG. 2

Substance KA-7038III formula III

Figure 3:
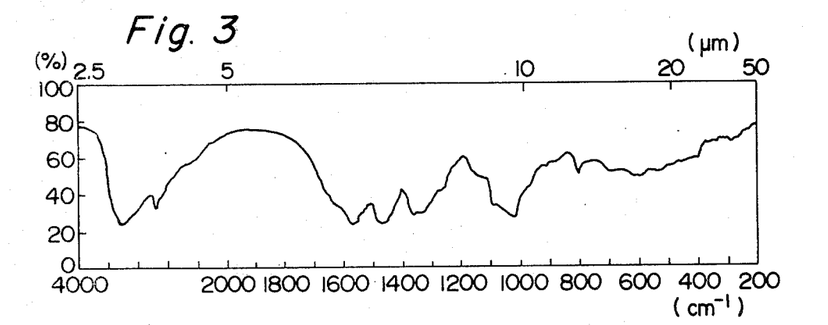

The chemical and physical properties of the substance KA-7038III are described below.
Molecular formula: $C_{15}H_{32}O_4N_4$.
Specific rotation: $[\alpha]_D^{25} +78°$ (c 1, $H_2O$).
Melting point: 74°–83° C.
IR spectrum: FIG. 3.

Substance KA-7038IV formula IV

Figure 4:
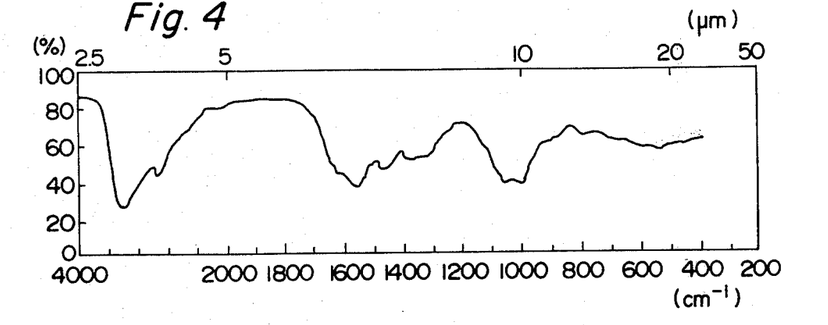

The chemical and physical properties of the substance KA-7038IV are described below.
Molecular formula: $C_{14}H_{30}O_5N_4$.
Specific rotation: $[\alpha]_D^{25} +115°$ (c 0.1, $H_2O$).
Melting point: 78°–82° C.
IR spectrum: FIG. 4.

Substance KA-7038V formula V

Figure 5:
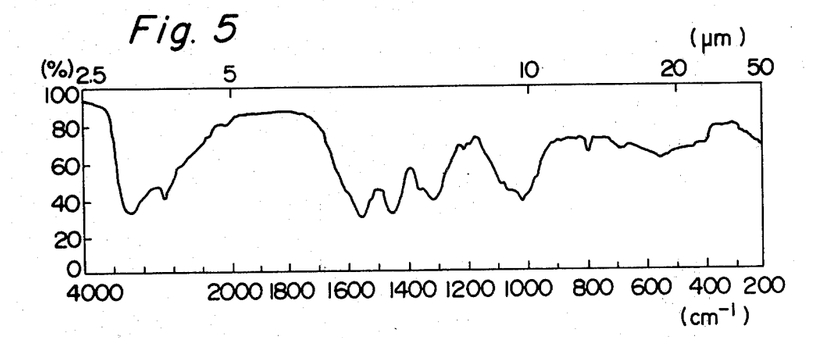

The chemical and physical properties of the substance KA-7038V are described below.
Molecular formula: $C_{14}H_{30}O_4N_4$.
Specific rotation: $[\alpha]_D^{25} +98°$ (c 0.5, $H_2O$).
IR spectrum: FIG. 5.

Substance KA-7038VI formula VI

Figure 6:
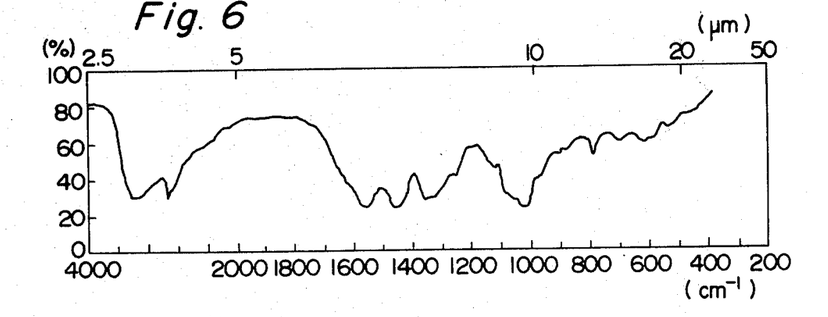

The chemical and physical properties of the substance KA-7038VI are described below.
Molecular formula: $C_{15}H_{32}O_4N_4$.
Specific rotation: $[\alpha]_D^{25} +58°$ (c 1, $H_2O$).
IR spectrum: FIG. 6.

Substance KA-7038VII formula VII

Figure 7:
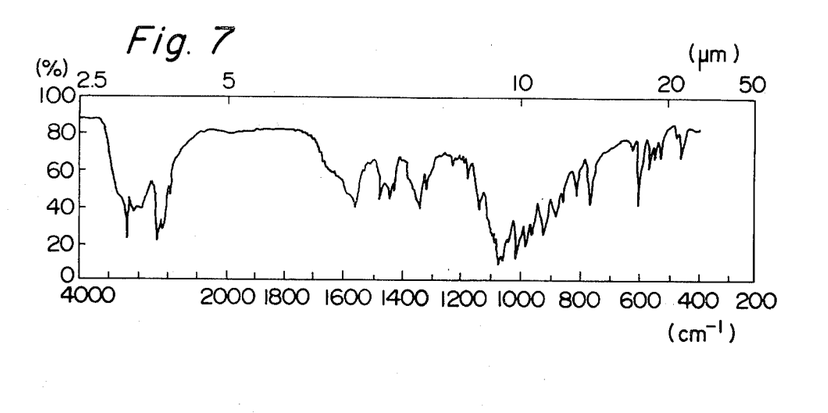

The chemical and physical properties of the substance KA-7038VII are described below.
Molecular formula: $C_{14}H_{30}O_4N_4$.
Specific rotation: $[\alpha]_D^{25} +59°$ (c 1, $H_2O$).
IR spectrum: FIG. 7.

The novel antibiotic of this invention can be produced by cultivating an antibiotic substance KA-7038-producing strain belonging to genus Streptomyces and isolating the antibiotic substance KA-7038 from the culture broth. If desired, one or more of the antibiotics substances KA-7038 I-VII can be separated from the resulting substance KA-7038.

The morphological, cultural and physiological characteristics of Streptomyces sp. strain KC-7038, a typical example of the KA-7038-producing strain, are shown below. Unless otherwise specified, its properties on various culture media were observed by ordinary methods after cultivating it for 21 days at 27° C. The colors were expressed for a mature culture in accordance with the classifications of "Color Harmony Manual" (Container Corp. Amer. 1958).

I. Morphological properties

This strain produces both substrate hyphae and aerial hyphae. The aerial mycelium is simply branched. The chain of mature spores formed compact spirals. The spirals are formed in two to three turns. No formation of sporangium is observed. The spores are oval to cylindrical, 0.5–0.6 microns by 0.8–1.2 microns in size, and 20 or more of such spores are formed on each spore chain. The surface of the spore is slightly rough, but is considered as smooth (because no clear sclerotic granule is formed).

II. Cultural characteristics on various culture media

1. Sucrose-nitrate agar
   Growth: Poor, colorless
   Aerial mcycelium: Moderate, powdery, covert brown (2 li).
   Soluble pigment: None
2. Glucose-aspraragine agar
   Growth: Moderate, cream (1½ ca)
   Aerial mycelium: Moderate, powdery, white (a) to convert brown (2 li)
   Soluble pigment: None
3. Glycerol-asparagin agar
   Growth: Poor, colorless
   Aerial mycelium: Poor, powdery, white (a)
   Soluble pigment: None
4. Inorganic salt-starch agar
   Growth: Good, pearl (3 ba)
   Aerial mycelium: Good, powdery, white (a) to silver gray (3 fe)
   Soluble pigment: None
5. Tyrosine agar
   Growth: Good, ivory (2 db)
   Aerial mycelium: Moderate, powdery, white (a)
   Soluble pigment: None
6. Nutrient agar
   Growth: Good, buff (2 fb)
   Aerial mycelium: None
   Soluble pigment: None
7. Yeast extract-malt extract agar
   Growth: Good, light wheat (2 ea)
   Aerial mycelium: Poor, powdery, white (a)
   Soluble pigment: None
8. Oat meal agar
   Growth: Moderate, colorless
   Aerial mycelium: Good, powdery, convert brown (2 li)
   Soluble pigment: None
9. Peptone-yeast extract-iron agar
   Growth: Good, cream (1½ ca)
   Aerial mycelium: None
   Soluble pigment: Faint yellow

III. Physiological properties

1. Growth temperature range: 17° to 37° C.
2. Liquefaction of gelatin: Positive
3. Hydrolysis of starch: Positive
4. Action on milk: No growth
5. Formation of melanoid pigment: Negative

IV. Utilization of carbon sources

On a Pridham and Gottlieb agar medium, L-arabinose, D-xylose, D-glucose, D-fructose, sucrose, inositol, L-rhamnose, raffinose, and D-mannitol are not utilized. On a medium resulting from the removal of copper sulfate from the above culture medium, D-xylose and D-glucose are utilized.

V. Cell wall

LL-Diaminopimelic acid was formed as a component of the cell wall.

From the above properties, the strain KC-7038 is considered to belong to the genus Streptomyces. Species which contain spiral spore chains, white to gray aerial mycelia and spores with a smooth surface, and do not produce soluble pigment nor utilize inositol and sucrose have been screened from known strains described in Bergey's Manual of Determinative Bacteriology, 8th edition (1975), ISP strains of Shirling and Gottlieb, and "The Actinomycetes" by Waksman. As a result, Streptomyces argenteolus (ISP 5226), Streptomyces griseolosuffucus (IMET JA 3708), Streptomyces griseofuscus (ISP 5191) and Streptomyces pyridomyceticus (ISP 5024) have been located.

However, the strain KC-7038 clearly differs from Streptomyces argenteolus, Streptomyces griseolosuffucus and Streptomyces griseofuscus in the utilization of carbon sources excepting inositol and sucrose. On the other hand, the strain KC-7038 is common with Streptomyces pyridomyceticus in that it does not utilize all carbon sources on the Pridham and Gottlieb agar medium, but they are clearly different in the following respects.

The growth of Streptomyces pyridomyceticus is poorer than that of the strain KC-7038 on various media of ISP, and aerial mycelia is scarcely observed. The KC-7038 does not grow in a skim milk medium, and its liquefaction of gelatin is positive. In contrast, Streptomyces pyridomyceticus shows a negative result in liquefaction of gelatin, and grows in a skim milk medium. Furthermore they are different in the utilization of glucose and sucrose in a Pridham Gottlieb medium from which copper sulfate has been removed. The metabolites resulting from these also differ from each other.

From these results, it has been concluded that the present strain falls into none of the known species, and is a novel species. The present inventors have named it Streptomyces sp. KC-7038.

The strain used in this invention can be mutated by an artificial mutating means using ultraviolet light, X-rays, various chemicals such as nitrosoguanidines, nitrosourea or mitomycin, etc. All such mutants which have the ability to produce the antibiotic substance KA-7038 can be used in this invention.

According to this invention, there is also provided a biologically pure culture of Streptomyces sp. KC-7038 having characteristics identified as FERM-P No. 4388, ATCC number 31530, and also having the ability to produce antibiotic substance KA-7038 by fermentation in a nutrient medium containing a carbon source, a nitrogen source and minerals.

Suitable culture media for use in fermenting the KA-7038-producing strain of the genus streptomyces comprise carbon and nitrogen sources and as optional ingredients, inorganic salts (minerals), very small amounts of heavy metals, etc.

Various carbon sources can be used, and examples of preferred carbon sources are glucose, starch, sucrose, fructose, dextrin, molasses and glycerol, which can be used either alone or as suitable mixtures. Hydrocarbons, alcohols, organic acids and vegetable oils can also be used if the strain used can utilize them as a carbon source.

Examples of nitrogen sources are soybean meal, yeast extract, dried yeast, peptone, meat extract, corn steep liquor, Casamino acid, Distiller's soluble, ammonium chloride, ammonium sulfate, ammonium nitrate, urea and sodium nitrate, which can be used either alone or as suitable mixtures. Examples of inorganic salts include sodium chloride, nitrates, calcium carbonate, potassium chloride, cobalt chloride and ferrous sulfate.

Inorganic substances and organic substances (e.g., amino acids) which aid in the growth of the strain and promote the production of substance KA-7038 can also be added to the culture medium as required. When an aerating cultivation method is employed, an antifoamer such as fatty acid oils, silicone oils, cotton seed oil and paraffins can also be added to the culture medium.

Cultivation may be carried out in a solid medium. Preferably, however, the same as in the general process for producing antibiotics, a liquid cultivating method, especially a submerged cultivation method, is used. The cultivation is carried out under aerobic conditions, and the cultivation temperature is preferably about 20° to about 35° C., more preferably about 24° to about 27° C. Preferably, during the cultivation, the pH of the culture medium is maintained at about 4 to about 10. The cultivation period is generally about 2 days to about 10 days.

As a result of the cultivation, the substance KA-7038 is produced and accumulated in the culture broth. When the amount of the substance KA-7038 produced in the culture broth reaches a maximum, the cultivation is stopped. The substance KA-7038 can be collected from the culture broth.

Since the substance KA-7038 is a water-soluble basic substance soluble in water but difficultly soluble in common organic solvents, it can be separated from the culture broth by utilizing the procedures which are customarily used in isolating and purifying water-soluble basic antibiotics. For example, there can be used an adsorption-desorption method using an ion exchange resin, active carbon etc.; column chromatographic method using cellulose, silica gel, alumina, etc.; and a method for extracting with butanol, amyl alcohol, etc. using a higher fatty acid as an adjuvant.

For example, if the culture broth filtrate is charged on a column of a weak acidic cation exchange resin, the substance KA-7038 is adsorbed on it. The substance KA-7038 is then isolated by elution with a 0.1–0.3 N alkali or acid. The resulting active eluate may be lyophilized to afford a crude powder of substance KA-7038.

Examples of the weak acidic cation exchange resin used to recover the substance KA-7038 are Amberlite IRC-50, IRC-84 and CG-50 (Rohm & Haas Co.); and Diaion WK-10 and WK-20 (Mitsubishi Chemical Co., Ltd.). Examples of alkalies that can be used for the elution are ammonium hydroxide solution, and an aqueous solution of sodium hydroxide. Examples of the acids are formic acid, hydrochloric acid and sulfuric acid. Another example of the recovering method comprises adjusting the pH of the culture broth filtrate to 7 to 9, contacting the filtrate with active carbon to cause the substance KA-7038 to adsorb on the active carbon, and eluting the substance with acidic water.

The substance KA-7038 that can be isolated by the methods described above can be separated into KA-7038 I, II, III, IV, V, VI and VII by dissolving it in water, charging it on a column of an adsorbent such as a weak acidic ion exchange resin of the type described above or a weak acidic ion exchanger such as CM-sephadex or CM-cellulose to cause the substance to be adsorbed on the adsorbent, and then eluting it with an alkaline aqueous solution such as dilute ammonium hydroxide, or an aqueous solution of ammonium carbonate or ammonium formate by a gradient method or a stepwise method. According to this separating procedure, substance KA-7038 VII, substance KA-7038 VII, substance KA-7038 I, substance KA-7038 II, substance KA-7038 VI, substance KA-7038 III and substance KA-7038 V as free bases are separated successively.

The resulting substances KA-7038 I, II, III, IV, V, VI and VII thus separated can be obtained in powder form by concentrating the eluate and lyophilizing the condensate. They can be purified by column chromatography on, for example, cellulose or strong basic anion exchange resin, by, for example, dissolving the powder in water, causing them to be adsorbed on a column of a strong basic anion exchange resin such as Dowex 1×2 (Dow Chemical), eluting them with deionized water, collecting active fractions, and lyophilizing the collected fractions. These substances KA-7038 obtained as free bases can be converted to their acid addition salts by treatment with pharmaceutically acceptable inorganic or organic acids. Examples of such acids are inorganic acids such as sulfuric acid, hydrochloric acid, hydroiodic acid, phosphoric acid, carbonic acid, nitric acid etc., and organic acids such as acetic acid, fumaric acid, maleic acid, citric acid, mandelic acid and succinic acid.

The substance KA-7038 III has the structural formula of the substance KA-7038 I in which the glycyl group —COCH$_2$NH$_2$ is split off. Therefore, the substance KA-7038 III can also be obtained by treating the substance KA-7038 I with alkalides or acids to decompose the substance KA-7038 I and convert it to substance KA-7038 III. This conversion can be effected by treating the substance KA-7038 I with a 0.1–4 N aqueous solution of an alkaline reagent such as sodium hydroxide or barium hydroxide or with a 0.1–1 N aqueous solution of an acidic reagent such as hydrochloric acid or sulfuric acid.

In the case of using the alkaline reagent, a strong basic anion exchange resin [e.g., Amberlite IRA 400 (OH$^-$ form) or Dowex 1×2 (OH$^-$ form)] may be added, and the reaction can be performed in the suspended state. Likewise, when the acidic reagent is used, a strong acidic cation exchange resin such as Amberlite 1R 120 (H$^+$ form) or Dowex 50×8 (H$^+$ form) may be added, and the reaction can be performed in the suspended state. The reaction can be performed usually at about 30° to 100° C. for about 0.5 to 3 hours.

The physical and chemical properties of the novel antibiotics substances KA-7038 I-VII are described in more detail below.

Substance KA-7038 I (free base)

(1) Nature: White powder
(2) Molecular formula: C$_{17}$H$_{35}$O$_5$N$_5$
(3) Elemental analysis:

|  | C | H | N |
| --- | --- | --- | --- |
| Calculated (%) | 52.42 | 9.06 | 17.98 |
| Found (%) | 51.98 | 8.71 | 17.64 |

(4) Molecular weight: 389 (mass spectrum)
(5) Melting point: 83°–90° C.
(6) Specific rotation: $[\alpha]_D^{25}+120.5°$ (c 1, H$_2$O)
(7) Ultraviolet absorption spectrum: At 220–360 mm, no characteristic absorption is shown, and only a terminal absorption exists.
(8) Infrared absorption spectrum: The infrared absorption spectrum of a sample in potassium bromide tablet is as shown in FIG. 1.
(9) Solubility: Very readily soluble in water. Easily soluble in methanol, little soluble in ethanol, slightly soluble in acetone. Insoluble in chloroform, ethyl acetate, diethyl ether, hexane and petroleum ether.
(10) Color reaction: Ninhydrin reaction and Rydon Smith reaction-positive; Sakaguchi reaction, ferric chloride reaction and Fehling reaction-negative;
(11) Stability: Stable at a pH of 2.0 to 8.0.
(12) Nuclear magnetic resonance spectrum ($\delta_{D2O}$, ppm):
  2.75 (3H, s, 6'- N-C$\underline{H}_3$)
  3.12 (3H, s, 4- N-C$\underline{H}_3$)
  3.45 (3H, s, OCH$_3$)
  4.06 (2H, s, COC$\underline{H}_2$N)
  5.32 (1H, d, M=3.5 Hz, anomeric $\underline{H}$)

(13) Mass spectrum (m/e): 390 (M$^+$+1), 360, 276, 258, 230, 143
(14) Paper chromatogrophy:
  Rf value: 0.86
  Filter paper: Whatman No. 1
  Solvent: a lower layer of chloroform-methanol-17% ammonium hydroxide (2:1:1)
(15) Thin-layer chromatography: TLC aluminum sheet (silica gel 60 R$_{254}$ 0.2 mm) (Merck & Co., Inc.) was used.

| Rf value | Solvent |
| --- | --- |
| 0.61 | Butanol-ethanol-chloroform-17% ammonium hydroxide (4:5:2:5) |
| 0.60 | Chloroform-methanol-17% ammonium hydroxide (1:8:3) |
| 0.16 | A lower layer of chloroform-methanol-17% ammonium hydroxide (2:1:1) |
| 0.87 | An upper layer of chloroform-methanol-17% ammonium hydroxide (2:1:1) |

Substance KA-7038 II (free base)

(1) Nature: White powder
(2) Molecular formula: C$_{13}$H$_{28}$O$_4$N$_4$
(3) Elemental analysis:

|  | C | H | N |
| --- | --- | --- | --- |
| Calculated | 51.30 | 9.27 | 18.41 |
| Found (%) | 51.12 | 8.87 | 18.10 |

(4) Molecular weight: 304 (mass spectrum)
(5) Melting point: 8.5°–102° C.
(6) Specific rotation: $[\alpha]_D^{25}+61°$ (c 1, H$_2$O)
(7) Ultraviolet absorption spectrum: At 220–360 nm, no characteristic absorption is shown, but only a terminal absorption exists.
(8) Infrared absorption spectrum: The infrared absorption spectrum of a sample in potassium bromide tablet is as shown in FIG. 2.
(9) Solubility: Very readily soluble in water. Easily soluble in methanol, little soluble in ethanol, slightly soluble in acetone. Insoluble in chloroform, ethyl acetate, diethyl ether, hexane and petroleum ether.
(10) Color reaction: Ninhydrin reaction and Rydon Smith reaction-positive; Sakaguchi reaction, ferric chloride reaction and Fehling reaction-negative;
(11) Stability: Stable at a pH of 2.0 to 9.0.
(12) Nuclear magnetic resonance spectrum ($\delta_{D2O}$, ppm):
  2.83 (3H, s, N-C$\underline{H}_3$)
  5.84 (1H, d, J=3.5 Hz, anomeric H)
(13) Mass spectrum (m/e): 305 (M$^+$+1), 214, 205, 177, 129
(14) Paper chromatography:
  Rf value: 0.18
  Filter paper: Whatman No. 1
  Solvent: a lower layer of chloroform-methanol-17% ammonium hydroxide (2:1:1).
(15) Thin-layer chromatography: TLC aluminum sheet (silica gel 60 R$_{254}$ 0.2 mm) (Merck & Co., Inc.) was used.

| Rf value | Solvent |
| --- | --- |
| 0.43 | Butanol-ethanol-chloroform-17% ammonium hydroxide (4:5:2:5) |
| 0.44 | Chloroform-methanol-17% ammonium hydroxide |

| Rf value | Solvent |
|---|---|
| | (1:8:3) |
| 0.06 | A lower layer of chloroform-methanol-17% ammonium hydroxide (2:1:1) |
| 0.73 | An upper layer of chloroform-methanol-17% ammonium hydroxide (2:1:1) |

Substance KA-7038 III (free base)

(1) Nature: White powder
(2) Molecular formula: $C_{15}H_{32}O_4N_4$
(3) Elemental analysis:

| | C | H | N |
|---|---|---|---|
| Calculated (%) | 54.19 | 9.70 | 16.85 |
| Found (%) | 53.84 | 9.38 | 16.50 |

(4) Molecular weight: 332 (mass spectrum)
(5) Melting point: 74°–83° C.
(6) Specific rotation: $[\alpha]_D^{25} +78°$ (c 0.5, $H_2O$)
(7) Ultraviolet absorption spectrum: At 220–360 nm, no characteristic absorption is shown, but only a terminal absorption exists.
(8) Infrared absorption spectrum: The infrared absorption spectrum of a sample in potassium bromide tablet is as shown in FIG. 3.
(9) Solubility: Very readily soluble in water. Easily soluble in methanol, little soluble in ethanol, slightly soluble in acetone. Insoluble in chloroform, ethyl acetate, diethyl ether, hexane and petroleum ether.
(10) Color reaction: Ninhydrin reaction and Rydon Smith reaction-positive; Sakaguchi reaction, ferric chloride reaction and Fehling reaction-negative;
(11) Stability: Stable at a pH of 2.0 to 9.0.
(12) Nuclear magnetic resonance spectrum ($\delta_{D_2O}$, ppm): as HCl salt.
 2.73 (3H, s, 6'- N-C$\underline{H}_3$)
 2.83 (3H, s, 4- N-C$\underline{H}_3$)
 3.46 (3H, s, OC$\underline{H}_3$)
 5.43 (1H, d, J=3.5 Hz, anomeric $\underline{H}$)
(13) Mass spectrum (m/e): 333 (M$^+$+1), 332, 283, 230, 219, 191, 143
(14) Paper chromatography:
 Rf value: 0.92
 Filter paper: Whatman No. 1
 Solvent: a lower layer of chloroform-methanol-17% ammonium hydroxide (2:1:1).
(15) Thin-layer chromatography: TLC aluminum sheet (silica gel 60 $F_{254}$ 0.2 mm) (Merck & Co., Inc.) was used.

| Rf value | Solvent |
|---|---|
| 0.65 | Butanol-ethanol-chloroform-17% ammonium hydroxide (4:5:2:5) |
| 0.61 | Chloroform-methanol-17% ammonium hydroxide (1:8:3) |
| 0.35 | A lower layer of chloroform-methanol-17% ammonium hydroxide (2:1:1) |
| 0.84 | An upper layer of chloroform-methanol-17% ammonium hydroxide (2:1:1) |

Substance KA-7038 IV (free base)

(1) Nature: White powder
(2) Molecular formula: $C_{14}H_{30}O_5N_4$
(3) Elemental analysis:

| | C | H | N |
|---|---|---|---|
| Calculated (%) | 50.28 | 9.04 | 16.75 |
| Found (%) | 49.89 | 8.91 | 16.45 |

(4) Molecular weight: 334 (mass spectrum)
(5) Melting point: 78°–82° C.
(6) Specific rotation: $[\alpha]_D^{25} +115°$ (c 0.1, $H_2O$)
(7) Ultraviolet absorption spectrum: At 220–360 nm, no characteristic absorption is shown, but only a terminal absorption exists.
(8) Infrared absorption spectrum: The infrared absorption spectrum of a sample in potassium bromide tablet is as shown in FIG. 4.
(9) Solubility: Very readily soluble in water. Easily soluble in methanol, little soluble in ethanol, slightly soluble in acetone. Insoluble in chloroform, ethyl acetate, diethyl ether, hexane and petroleum ether.
(10) Color reaction: Ninhydrin reaction and Rydon Smith reaction-positive; Sakaguchi reaction, ferric chloride reaction and Fehling reaction-negative;
(11) Stability: Stable at a pH of 2.0 to 8.0.
(12) Nuclear magnetic resonance spectrum ($\delta_{D_2O}$, ppm):
 (As free base)
  2.47 (3H, s, N-C$\underline{H}_3$)
  3.43 (3H, s, O-C$\underline{H}_3$)
  5.08 (1H, d, anomeric $\underline{H}$)
 (As HCl salt)
  2.72 (3H, s, N-C$\underline{H}_3$)
  3.37 (3H, s, O-C$\underline{H}_3$)
  5.44 (1H, d, anomeric $\underline{H}$)
(13) Mass spectrum (m/e): 335 (M$^+$+1), 235, 207, 189, 129
(14) Paper chromatography:
 Rf value: 0.63
 Filter paper: Whatman No. 1
 Solvent: a lower layer of chloroform-methanol-17% ammonium hydroxide (2:1:1).
(15) Thin-layer chromatography: TLC aluminum sheet (silica gel 60 $F_{254}$ 0.2 mm) (Merck & C0., Inc.) was used.

| Rf value | Solvent |
|---|---|
| 0.56 | Butanol-ethanol-chloroform-17% ammonium hydroxide (4:5:2:5) |
| 0.62 | Chloroform-methanol-17% ammonium hydroxide (1:8:3) |
| 0.13 | A lower layer of chloroform-methanol-17% ammonium hydroxide (2:1:1) |
| 0.85 | An upper layer of chloroform-methanol-17% ammonium hydroxide (2:1:1) |

Substance KA-7038 V (free base)

(1) Nature: White powder
(2) Molecular formula: $C_{14}H_{30}O_4N_4$
(3) Elemental analysis:

| | C | H | N |
|---|---|---|---|
| Calculated (%) | 52.81 | 9.50 | 17.60 |
| Found (%) | 52.70 | 9.33 | 17.41 |

(4) Molecular weight: 318 (mass spectrum)
(5) Specific rotation: $[\alpha]_D^{25} +98°$ (c 0.5, $H_2O$)

(6) Ultraviolet absorption spectrum: At 220–360 nm, no characteristic absorption is shown, but only a terminal absorption exists.
(7) Infrared absorption spectrum: The infrared absorption spectrum of a sample in potassium bromide tablet is as shown in FIG. 5.
(8) Solubility: Very readily soluble in water. Easily soluble in methanol, little soluble in ethanol, slightly soluble in acetone. Insoluble in chloroform, ethyl acetate, diethyl ether, hexane and petroleum ether.
(9) Color reaction: Ninhydrin reaction and Rydon Smith reaction-positive; Sakaguchi reaction, ferric chloride reaction and Fehling reaction-negative;
(10) Stability: Stable at a pH of 2.0 to 9.0.
(11) Nuclear magnetic resonance spectrum ($\delta_{D_2O}$, ppm):
(As free base)
2.35 (3H, s, N-C$\underline{H_3}$)
3.36 (3H, s, O-C$\underline{H_3}$)
5.12 (1H, d, anomeric $\underline{H}$)
(As HCl salt)
2.78 (3H, s, N-C$\underline{H_3}$)
3.43 (3H, s, O-C$\underline{H_3}$)
5.76 (1H, d, anomeric $\underline{H}$)
(12) Mass spectrum (m/e): 319 (M$^+$+1), 219, 191, 173, 129
(13) Paper chromatography:
Rf value: 0.82
Filter paper: Whatman No. 1
Solvent: a lower layer of chloroform-methanol-17% ammonium hydroxide (2:1:1).
(14) Thin-layer chromatography: TLC aluminum sheet (silica gel 60 F$_{254}$ 0.2 mm) (Merck & Co., Inc.) was used.

| Rf value | Solvent |
| --- | --- |
| 0.57 | Butanol-ethanol-chloroform-17% ammonium hydroxide (4:5:2:5) |
| 0.55 | Chloroform-methanol-17% ammonium hydroxide (1:8:3) |
| 0.25 | A lower layer of chloroform-methanol-17% ammonium hydroxide (2:1:1) |
| 0.81 | An upper layer of chloroform-methanol-17% ammonium hydroxide (2:1:1) |

Substance KA-7038 VI (free base)

(1) Nature: White powder
(2) Molecular formula: C$_{15}$H$_{32}$O$_4$N$_4$
(3) Elemental analysis:

|  | C | H | N |
| --- | --- | --- | --- |
| Calculated (%) | 54.19 | 9.70 | 16.85 |
| Found (%) | 53.83 | 9.87 | 16.59 |

(4) Molecular weight: 332 (mass spectrum)
(5) Specific rotation: $[\alpha]_D^{25}$ +58° (c 1, H$_2$O)
(6) Ultraviolet absorption spectrum: At 220–360 nm, no characteristic absorption is shown, but only a terminal absorption exists.
(7) Infrared absorption spectrum: The infrared absorption spectrum of a sample in potassium bromide tablet is as shown in FIG. 6.
(8) Solubility: Very readily soluble in water. Easily soluble in methanol, little soluble in ethanol, slightly soluble in acetone. Insoluble in chloroform, ethyl acetate, diethyl ether, hexane and petroleum ether.
(9) Color reaction: Ninhydrin reaction and Rydon Smith Reaction-positive; Sakaguchi reaction, ferric chloride reaction and Fehling reaction-negative;
(10) Stability: Stable at a pH of 2.0 to 8.0.
(11) Nuclear magnetic resonance spectrum ($\delta_{D_2O}$, ppm):
2.87 (3H, s, 6'-N-C$\underline{H_3}$)
2.93 (3H, s, 4-N-C$\underline{H_3}$)
3.87 (3H, s, O-C$\underline{H_3}$)
5.57 (1H, d, anomeric $\underline{H}$)
(12) Mass spectrum (m/e): 333 (M$^+$+1), 332, 283, 230, 219, 191, 143
(13) Paper chromatography:
Rf value: 0.91
Filter paper: Whatman No. 1
Solvent: a lower layer of chloroform-methanol-17% ammonium hydroxide (2:1:1).
(14) Thin-layer chromatography: TLC aluminum sheet (silica gel 60 F$_{254}$ 0.2 mm) (Merck & Co., Inc.) was used.

| Rf value | Solvent |
| --- | --- |
| 0.63 | Butanol-ethanol-chloroform-17% ammonium hydroxide (4:5:2:5) |
| 0.60 | Chloroform-methanol-17% ammonium hydroxide (1:8:3) |
| 0.29 | A lower layer of chloroform-methanol-17% ammonium hydroxide (2:1:1) |
| 0.62 | An upper layer of chloroform-methanol-17% ammonium hydroxide (2:1:1) |

Substance KA-7038 VII (free base)

(1) Nature: White powder
(2) Molecular formula: C$_{14}$H$_{30}$O$_4$N$_4$
(3) Elemental analysis:

|  | C | H | N |
| --- | --- | --- | --- |
| Calculated (%) | 52.81 | 9.50 | 17.60 |
| Found (%) | 52.50 | 9.78 | 17.41 |

(4) Molecular weight: 318 (mass spectrum)
(5) Specific rotation: $[\alpha]_D^{25}$ +59° (c 1, H$_2$O)
(6) Ultraviolet absorption spectrum: At 220–360 nm, no characteristic absorption is shown, but only a terminal absorption exists.
(7) Infrared absorption spectrum: The infrared absorption spectrum of a sample in potassium bromide tablet is as shown in FIG. 7.
(8) Solubility: Very readily soluble in water. Easily soluble in methanol, little soluble in ethanol, slightly soluble in acetone. Insoluble in chloroform, ethyl acetate, diethyl ether, hexane and petroleum ether.
(9) Color reaction: Ninhydrin reaction and Rydon Smith reaction-positive; Sakaguchi reaction, ferric chloride reaction and Fehling reaction-negative;
(10) Stability: Stable at a pH of 2.0 to 9.0.
(11) Nuclear magnetic resonance spectrum ($\delta_{D_2O}$, ppm):
2.92 (3H, s, N-C$\underline{H_3}$)
3.93 (3H, s, O-C$\underline{H_3}$)
5.63 (1H, d, anomeric $\underline{H}$)
(12) Mass spectrum (m/e): 319 (M$^+$+1), 219, 191, 173, 129
(13) Paper chromatography:
Rf value: 0.65
Filter paper: Whatman No. 1
Solvent: a lower layer of chloroform-methanol-17% ammonium hydroxide (2:1:1).

(14) Thin-layer chromatography: TLC aluminum sheet (silica gel 60 $F_{254}$ 0.2 mm) (Merck & Co., Inc.) was used.

| Rf value | Solvent |
|---|---|
| 0.62 | Butanol-ethanol-chloroform-17% ammonium hydroxide (4:5:2:5) |
| 0.61 | Chloroform-methanol-17% ammonium hydroxide (1:8:3) |
| 0.28 | A lower layer of chloroform-methanol-17% ammonium hydroxide (2:1:1) |
| 0.63 | An upper layer of chloroform-methanol-17% ammonium hydroxide (2:1:1) |

The Rf values by paper chromatography of the novel antibiotics substance KA-7038 I-VII are shown in Table 1 below in comparison with those of known antibiotics. Similar data obtained by thin-layer chromatography are shown in Table 2 below.

The substance KA-7038 has been found to differ greatly in physicochemical properties from kanamycins A, B and C, tobramycin, paromomycin, neomycins A, B and C, butirosins A and B, lividomycins A and B, ribostamycin, xylostatin, apramycin, gentamicins A and B, and sorbistin, and antibiotic substance No. 460, which are known dextrorotatory water-soluble basic antibiotic substances. Furthermore, the substance KA-7038 differs from the known antibiotics shown in Tables 1 and 2 in $R_f$ values determined by paper chromatography and thin layer chromatography.

TABLE 1

Rf values of the substances KA-7038 and known antibiotics
Solvent system: a lower layer of chloroform-methanol-17% ammonium hydroxide (2:1:1)
Filter paper: Whatman No. 1

| Antiobiotics | Rf value |
|---|---|
| KA-7038I | 0.86 |
| KA-7038II | 0.18 |
| KA-7038III | 0.92 |
| KA-7038IV | 0.63 |
| KA-7038V | 0.82 |
| KA-7038VI | 0.91 |
| KA-7038VII | 0.65 |
| KA-6606I | 0.53 |
| KA-6606II | 0.86 |
| KA-6606III | 0.27 |
| KA-6606IV | 0.55 |
| KA-6606V | 0.91 |
| KA-6606VI | 0.94 |
| Gentamicin $C_1$ | 0.59 |

TABLE 1-continued

Rf values of the substances KA-7038 and known antibiotics
Solvent system: a lower layer of chloroform-methanol-17% ammonium hydroxide (2:1:1)
Filter paper: Whatman No. 1

| Antiobiotics | Rf value |
|---|---|
| Gentamicin $C_2$ | 0.35 |
| Gentamicin $C_{1a}$ | 0.12 |
| Sagamicin | 0.49 |
| Sisomicin | 0.12 |
| Verdamicin | 0.35 |
| G-52 | 0.49 |
| Fortimicin A | 0.32 |
| Fortimicin B | 0.89 |
| Others (*1) | 0.0–0.05 |

(*1) Others represent kanamycin A, B and C, paromomycin, neomycin A, B and C, butirosins A and B, lividomycin A and B, ribostamycin, xylostatin, gentamicin A and B, tobramycin, apramycin, sorbistin, antibiotic substance 460, hygromycin, or destomycin.

TABLE 2

Rf values of the substances KA-7038 and known antibiotics
Solvent system
Solvent a: Butanol-ethanol-chloroform-17% ammonium hydroxide (4:5:2:5)
Solvent b: Chloroform-methanol-17% ammonium hydroxide (1:8:3)
Plate
TLC aluminum sheet (silica gel 60 $F_{254}$ 0.2 mm) (Merck & Co., Inc.)

| Antibiotics | Rf value Solvent a | Solvent b |
|---|---|---|
| KA-7038I | 0.61 | 0.60 |
| KA-7038II | 0.43 | 0.44 |
| KA-7038III | 0.65 | 0.61 |
| KA-7038IV | 0.56 | 0.62 |
| KA-7038V | 0.57 | 0.55 |
| KA-7038VI | 0.63 | 0.60 |
| KA-7038VII | 0.62 | 0.61 |
| KA-6606I | 0.56 | 0.60 |
| KA-6606II | 0.57 | 0.52 |
| KA-6606III | 0.55 | 0.64 |
| KA-6606IV | 0.56 | 0.66 |
| KA-6606V | 0.64 | 0.61 |
| KA-6606VI | 0.69 | 0.73 |
| Gentamicin $C_1$ | 0.52 | 0.40 |
| Gentamicin $C_2$ | 0.51 | 0.44 |
| Gentamicin $C_{1a}$ | 0.43 | 0.34 |
| Sagamicin | 0.45 | 0.32 |
| Fortimicin A | 0.53 | 0.56 |
| Fortimicin B | 0.60 | 0.70 |

The antimicrobial spectra of the novel antibiotics substances KA-7038 I-VII are shown in Table 3.

TABLE 3

| | I | II | III | IV | V | VI | VII |
|---|---|---|---|---|---|---|---|
| Staphylococcus aureus 209P | 1.5 | 50 | 25 | 25 | 50 | 25 | 50 |
| Staphylococcus aureus Smith | 0.4 | 25 | 6 | 12 | 25 | 6 | 25 |
| Bacillus subtilis ATCC 6633 | 0.2 | 6 | 12 | 3 | 3 | 12 | 6 |
| Bacillus cereus | 3 | 100 | 100 | 50 | 50 | 100 | 50 |
| Bacillus anthracis | 0.4 | 3 | 6 | 1.5 | 1.5 | 6 | 3 |
| Streptococcus feacalis | >100 | >100 | >100 | >100 | >100 | >100 | >100 |
| Escherichia coli NIHJ | 6 | 100 | 100 | 50 | 50 | 100 | 100 |
| Escherichia coli ML1410 | 12 | >100 | >100 | >100 | >100 | >100 | >100 |
| Escherichia coli ML1410R-81 (resistant to kanamycin, streptomycin and lividomycin) | 50 | >100 | >100 | >100 | >100 | >100 | >100 |
| Escherichia coli ML1410R-82 (resistant to kanamycin, streptomycin and butirosin) | 25 | >100 | >100 | >100 | >100 | >100 | >100 |
| Escherchia coli ML1410R-101 (resistant to gentamycin, tobramycin | 12 | >100 | >100 | >100 | >100 | >100 | >100 |

TABLE 3-continued

|  | I | II | III | IV | V | VI | VII |
|---|---|---|---|---|---|---|---|
| and kanamycin) |  |  |  |  |  |  |  |
| Proteus vulgaris OX19 | 6 | 100 | 100 | 50 | 50 | 100 | 100 |
| Klebisella pneumoniae PCI 602 | 6 | 100 | >100 | 100 | >100 | 100 | 100 |
| Pseudomonas aeruginosa Shibata | 6 | 100 | >100 | 100 | >100 | 100 | >100 |
| Proteus inconstans | 12 | >100 | >100 | >100 | >100 | >100 | >100 |
| Serratia sp. | 6 | >100 | >100 | >100 | >100 | >100 | >100 |
| Mycobacterium smegmatis ATCC 607 | 3 | >100 | >100 | >100 | >100 | >100 | >100 |

The acute toxicities of the substances KA-7038 I–VII of this invention determined by using mice are as follows:

| $LD_{50}$ | I | II | III | IV | V | VI | VII |
|---|---|---|---|---|---|---|---|
| (mg/kg) iv. | >100 | >300 | >300 | >300 | >300 | >300 | >300 |
| (mg/kg) sc. | >400 | >600 | >600 | >600 | >600 | >600 | >600 |

According to this invention, there can also be provided an antibiotic composition composed of (i) an antibiotically effective amount of an antibiotic substance KA-7038 selected from the group consisting of compounds having the formula I–VII indicated before, mixtures thereof and pharmaceutically acceptable acid addition salts thereof and (ii) a pharmaceutically acceptable diluent or carrier.

The amount of the compound (i) is, for example, about 0.01 to about 99.5% by weight, based on the weight of the composition.

The antibiotic composition of this invention may be in any dosage forms usually employed, but injectable preparations and capsules are especially preferred.

Preferably, like known water-soluble basic actibiotics, an preparation is prepared by filling a lyophilized powder of the antibiotic into a vial, preferably together with a stabilizer, and in use, the contents of the vial are dissolved in a dissolving liquid for administration.

The diluent or carrier includes, for example, liquid diluents such as distilled water for injection and physiological isotonic solution, and solid carriers such as lactose, starch, white sugar, glucose, crystalline cellulose, calcium carbonate, kaolin, D-mannitol, magnesium metasilicate aluminate, calcium sulfate, calcium phosphate and bentonite. Addition of stabilizers such as acidic sodium bisulfite is also preferred.

The dosage of the antibiotic substance of this invention can be suitably selected, and is, for example, about 0.01 to about 100 mg/kg/day.

Thus, according to this invention, there can be provided antibiotic compositions for animals other than humans, such as poultry, domesticated animals and cultivated fish, and also antibiotic compositions for human. These compositions are useful as antibacterial agents having a broad antibacterial spectrum.

The substance KA-7038 of this invention is also useful as a material for producing its derivatives.

The following Examples illustrate the present invention in greater detail.

EXAMPLE 1

Streptomyces KC-7038 strain was inoculated in a sterilized culture medium composed of 4% starch, 0.5% soybean meal, 4% corn steep liquor, 0.05% magnesium sulfate heptahydrate, 0.3 sodium chloride and 0.1% calcium carbonate. (pH was adjusted to 7.0 before sterilization.) The strain was pre-cultivated for about 48 hours at 27° C. to form a first seed strain.

A 200-liter tank was charged with 100 liters of a culture medium obtained by adding 1% of cotton seed oil to the same culture medium as the one used to form the seed culture. Then, 500 ml of the first seed was inoculated, and cultivated for 4 days at 27° C. under aeration and stirring (220 rpm; the flow rate of air, 50 liters/min.).

After the fermentation, dilute sulfuric acid was added to the fermentation broth to adjust its pH to 2.0, and Dicalite (Dicalite Orient Co., Ltd) was added as a filter aid, and the mycelia were removed by filtration. A dilute aqueous solution of sodium hydroxide was added to the filtrate to adjust its pH to 6.2, and the filtrate was passed through a column of Amberlite IRC-50 ($NH_4^+$ form), a weak acidic cation exchange resin. After washing with water, the adsorbed material was eluted with 1 N ammonia solution. Active fractions were collected, concentrated under reduced pressure, and lyophilized to afford 9.7 g of a crude powder of substance KA-7038.

9.7 g of the crude powder was dissolved in 1 liter of distilled water, and the solution was adjusted to pH 7.0 with dilute sulfuric acid. The solution was then passed through a column (3×150 cm) of a cation exchange resin, CM-Sephadex C-25 ($NH_4^+$ form), followed by washing with water. The adsorbed material was eluted at a rate of 60 ml per hour using a concentration gradient method between 5 liters of 0.05 N ammonia solution and 5 liters of 0.5 N ammonia solution. The eluates were fractionated into fractions each having a volume of 30 ml. The activity of each fraction was measured by a paper disc method using an agar plate of Bacillus subtilis.

Active fractions Nos. 96 to 112 were lyophilized to afford 0.65 g of a crude powder containing substance KA-7038. Lyophilization of active fractions Nos. 113 to 134 afforded 0.4 g of a crude powder of substance KA-7038 I and substance KA-7038 VII. Lyophilization of fractions Nos. 135 to 149 afforded 0.36 g of a crude powder of a mixture of substance KA-7038 I, substance KA-7038 II and substance KA-7038 VI. Furthermore, 0.9 g of a free base of substance KA-7038 III was obtained from fractions Nos. 150 to 172.

Then, 0.12 g of a crude powder of substance KA-7038 V was obtained from active fractions Nos. 173 to 212.

A sample of the substance KA-7038 (0.65 g) was filled as a uniform layer on a column packed with 300 ml of cellulose powder. It was developed with a lower layer of a chloroform-methanol-17% ammonia solution mixture (2:1:1) as an eluent at a rate of 30 ml per hour. The eluate was fractionated into fractions each having a volume of 10 ml, and the activity of each fraction was measured in a similar manner to that described above. Active fractions were collected, concentrated to dryness, and filled as a uniform layer on a column packed with 160 ml of silica gel. Using the lower layer of a chloroform-methanol-17% ammonia solution (2:1:1) as an eluent, it was eluted at a rate of 30 ml per hour. The eluate was fractionated into fractions each having a volume of 3 ml, and the activity of each fraction was measured in a similar manner to that described above. Fractions containing substance KA-7038 IV which were eluted subsequent to the elution of one or two minor components were collected, and the solvent was distilled off under reduced pressure. The residue was dissolved in 20 ml of water, and passed through a column packed with 5 ml of a weak acidic cation exchange resin, CM-Sephadex C-25 ($NH_4^+$ form). After washing with water, the adsorbed material was eluted with 0.5 N ammonia solution, and active fractions were collected. Lyophilization of the active fractions gave 0.01 g of a free base of substance KA-7038 IV as a colorless amorphous powder.

A crude powder (0.4 g) of a mixture of substance KA-7038 I and substance KA-7038 VII was charged as a uniform layer on a column packed with 200 ml of cellulose, and chromatographed using the lower layer of a chloroform-methanol-17% ammonia solution (2:1:1) mixture as an eluent, whereupon substance KA-7038 I and then substance KA-7038 VII were eluted. The fraction containing substance KA-7038 VII was concentrated to dryness, and again dissolved in water. The solution was caused to be adsorbed on a column of 15 ml of a weak acidic cation exchange resin, CM-Sephadex C-25 ($NH_4^+$ form). After washing with water, the adsorbed material was eluted by a concentration gradient method between 300 ml of 0.04 N ammonia solution and 300 ml of 0.4 N ammonia solution. Fractions containing substance KA-7038 VII were collected, and lyophilized to afford 0.01 g of a free base of a colorless powder.

On the other hand, when fractions containing substance KA-7038 I were concentrated to dryness, 0.31 g of a crude powder of substance KA-7038 I was obtained. The crude powder was dissolved in distilled water, and caused to be adsorbed on a column packed with 1000 ml of a weak acidic cation exchange resin, CM-Sephadex C-25 ($NH_4^+$ form), followed by washing with water. The adsorbed material was eluted by a concentration gradient method between 2.25 liters of water and 2.25 liters of 0.5 N ammonia solution. The activity of each fraction was measured. Active fractions were collected, and lyophilized to afford 0.21 g of a free base of substance KA-7038 I as a colorless amorphous powder.

A mixture (0.26 g) of substance KA-7038 I, substance KA-7038 II and substance KA-7038 VI was charged as a uniform layer on a column packed with 300 ml of cellulose powder. It was eluted using the lower layer of a chloroform-methanol-17% ammonia solution mixture (2:1:1) at a rate of 30 ml per hour. The eluate was fractionated into fractions each having a volume of 10 ml. The activity of each fraction was measured by the same method as above. As a result, substance KA-7038 VI was first eluted, and then substance KA-7038 I and substance KA-7038 II were successively eluted.

Active fractions of substance KA-7038 II were collected, and the solvent was distilled off under reduced pressure. The residue was again dissolved in 20 ml of water, and passed through a column packed with 5 ml of a weak acidic cation exchange resin, CM-Sephadex C-25 ($NH_4^+$ form). After washing with water, and adsorbed material was eluted with 0.5 N ammonia solution. Active fractions were collected, and lyophilized to afford 0.05 g of a free base of substance KA-7038 II as a colorless amorphous powder.

Fractions containing substance KA-7038 VI were collected, and the solvent was distilled off under reduced pressure. The residue was again dissolved in 100 ml of water, and passed through a column packed with 40 ml of a weak acidic cation exchange resin, CM-Sephadex C-25 ($NH_4^+$ form). After washing with water, the adsorbed material was eluted by a concentration gradient method between 500 ml of 0.1 N ammonia solution and 500 ml of 0.5 N ammonia solution. Fractions containing substance KA-7038 VI were collected, and lyophilized to afford 0.07 g of a free base of substance KA-7038 VI.

The crude powder (0.12 g) of substance KA-7038 V was dissolved in distilled water, and caused to be adsorbed on a column packed with 1000 ml of a weak acidic cation exchange resin, CM-Sephadex C-25 ($NH_4^+$ form). After washing with water, the adsorbed material was eluted by a concentration gradient method between 2.25 liters of water and 2.25 liters of 0.5 N ammonia solution.

The activity of each of the resulting fractions was measured in the same way as above. The active fractions were collected, and lyophilized to afford 0.02 g of a free base of substance KA-7038 V as a colorless amorphous powder.

EXAMPLE 2

The lyophilized powder of substance KA-7038 I obtained in Example 1 (100 g units) was dissolved in 500 ml of water, and dilute sulfuric acid was added to adjust the pH to 5.0-7.0. Lyophilization of the solution afforded 160 g of a powder of substance KA-7038 I, sulfate.

EXAMPLE 3

The lyophilized powder of substance KA-7038 I, sulfate (20 g units) and 200 mg of acidic sodium sulfite were uniformly mixed, and the mixture was poured into 100 vials. Each of the vials contained 200 mg (units) of substance KA-7038 I sulfate. Prior to use, the solution in a vial was dissolved in 2 to 5 ml of distilled water for injection. The solution can be administered intramuscularly or intravenously, or can be intravenously infused as a mixture with a nutrient infusion.

We claim:

1. An antibiotic substance KA-7038 selected from the group consisting of compounds having the following formulae, mixtures thereof and pharmaceutically acceptable acid addition salts thereof:

-continued

2. An antibiotic composition comprising (i) an antibiotically effective amount of an antibiotic substance KA-7038 selected from the group consisting of compounds having the following formulae, mixtures thereof and pharmaceutically acceptable acid addition salts thereof:

-continued and (ii) a pharmaceutically acceptable diluent or carrier.

3. An antibiotic substance of claim 1 wherein the pharmaceutically acceptable acid addition salts are salts of an acid selected from the group consisting of sulfuric acid, hydrochloric acid, hydroiodic acid, phosphoric acid, carbonic acid, nitric acid, acetic acid, fumaric acid, maleic acid, citric acid, mandelic acid and succinic acid.

4. An antibiotic composition of claim 2 wherein the pharmaceutically acceptable acid addition salts are salts of an acid selected from the group consisting of sulfuric acid, hydrochloric acid, hydroiodic acid, phosphoric acid, carbonic acid, nitric acid, acetic acid, fumaric acid, maleic acid, citric acid, mandelic acid and succinic acid.

5. The antibiotic composition of claim 2 wherein the amount of the antibiotic substance KA-7038 is about 0.01 to about 99.5% by weight based on the weight of the composition.

* * * * *